Figure 1:
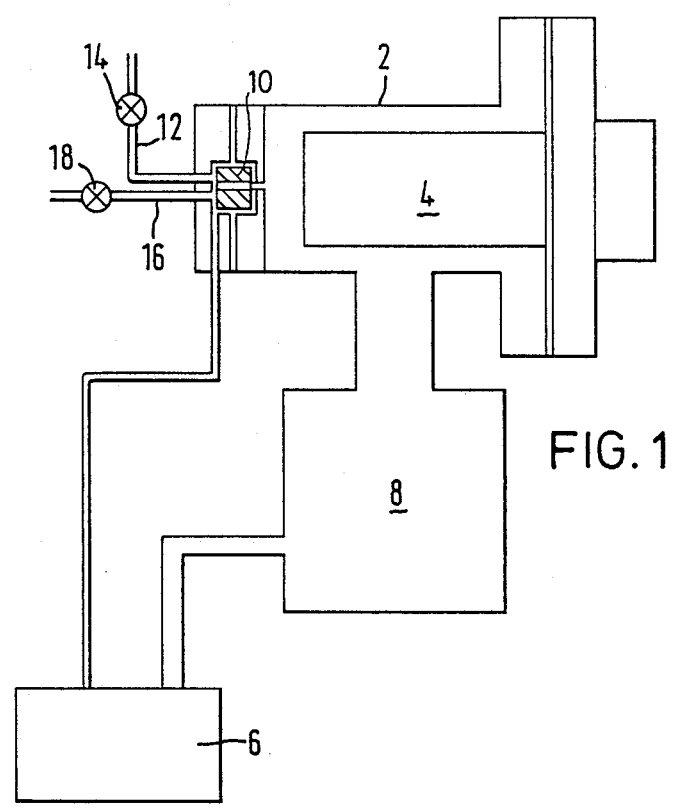

United States Patent [19]

Holme

[11] Patent Number: 4,810,877
[45] Date of Patent: Mar. 7, 1989

[54] MASS SPECTROMETER WITH MEANS TO CORRECT FOR THRESHOLD CARBON DIOXIDE

[75] Inventor: Alan E. Holme, Polegate, United Kingdom

[73] Assignee: The BOC Group, Inc., Montvale, N.J.

[21] Appl. No.: 917,627

[22] Filed: Oct. 10, 1986

[30] Foreign Application Priority Data

Oct. 14, 1985 [GB] United Kingdom ............... 8525290

[51] Int. Cl.⁴ .............................................. H01J 49/04
[52] U.S. Cl. .................................... 250/288; 250/281; 250/282
[58] Field of Search ............... 250/281, 282, 288, 291, 250/292

[56] References Cited

U.S. PATENT DOCUMENTS 3,700,893 10/1972 Seidenberg et al. ............ 250/288 A
4,558,708 12/1985 Labuda et al. ...................... 128/719

FOREIGN PATENT DOCUMENTS 3799823 12/1982 U.S.S.R. ................... 250/288

Primary Examiner—Carolyn E. Fields
Assistant Examiner—John A. Miller
Attorney, Agent, or Firm—Larry R. Cassett; Roger M. Rathbun

[57] ABSTRACT

A mass spectrometer adapted to monitor respiratory gases includes a spectrometer chamber arranged selectively to receive respiratory gas or an oxygen containing gas substantially free of carbon dioxide, together with means for correcting the detected level of carbon dioxide during respiration by that threshold level detected during the period when the mass spectrometer is responsive only to the oxygen containing gas.

14 Claims, 1 Drawing Sheet

MASS SPECTROMETER WITH MEANS TO CORRECT FOR THRESHOLD CARBON DIOXIDE

This invention relates to mass spectrometers and is directed to mass spectrometers adapted for use in anaesthesia.

Mass spectrometers are well known in the analysis of gases. Such mass spectrometers operate by utilising a stream of electrons accelerated from an electrically heated filament in an evacuated chamber, to ionise the gas under test which is slowly introduced or bled into the chamber through a suitable needle valve or other leak valve.

The ionised components of the gas to be analysed are accelerated to an anode of the mass spectrometer through an accurate path which may be varied electrostatically or magnetically to ensure that for a given electric or magnetic field as the case may be, only ions of a selected mass/charge ratio reach the anode for detection and measurement.

By calibrating the mass spectrometer, the existence or the concentration of specific ions present in the gas being analysed can be established by varying the electric or magnetic fields, either continuously or in discrete steps and the components of the gas analysed for display in any suitable mode.

It has been proposed to utilise a mass spectrometer to analyse the gas mixture inhaled and/or exhaled by a patient for example during anaesthesia. During such anaesthesia a carefully controlled quantity of an anaesthetic gas such as Ethrane (RTM) or Forane (RTM) is supplied to the patient, optionally together with an analgesic gas such as nitrous oxide eithe with or without oxygen.

The mass spectrometer may accordingly be adapted to monitor and measure the concentration of such gases both during the period of anaesthesia or other surgical procedure or for a period before or after anaesthesia to indicate the state of health or otherwise of the patient.

One gas which is particularly indicative of the health of the patient is carbon dioxide and it has accordingly been proposed in accordance with the present invention to specifically calibrate and to programme a mass spectrometer to monitor and to display the concentration of carbon dioxide in a patient's respiration.

In operation of a mass spectrometer, the mass spectrometer chamber is pumped typically to a pressure of $10^{-6}$ to $10^{-5}$ millibars generally by a combination of a rotary backing pump and a diffusion pump. Both such pumps contain oils and pumping fluids operating at temperatures above ambient and these generate hydrocarbon and other carbon containing vapours which combine with available oxygen to produce a background threshold level of carbon dioxide. This threshold level is also detected by the mass spectrometer and degrades the accuracy of and measurements of respiratory carbon dioxide alone.

It is one object of the present invention to produce a mass spectrometer which avoids this disadvantage.

The present invention according to its broadest aspect provides a method for monitoring respiratory gases by intermittently applying to the mass spectrometer, in the absence of respiratory gas, an oxygen containing gas substantially free of carbon dioxide, whereby to enable the oxygen to combine with residual carbon containing compounds derived from or through the pumping system, for the mass spectrometer and correcting the level of carbon dioxide measured during respiration by the threshold level measured arising during such combination.

The present invention according to a further aspect, provides a mass spectrometer adapted to monitor respiratory gases, the spectrometer chamber being arranged selectively to receive respiratory gas or a oxygen containing gas substantially free of carbon dioxide, together with means of correcting the detected level of carbon dioxide during respiration by that threshold level detected during the period when the mass spectrometer is responsive only to the oxygen containing gas.

Preferably the oxygen containing gas is air which is bled into the mass spectrometer chamber through a suitable needle or other leak valve.

Conveniently the mass spectrometer chamber is provided with two flow valve controlled inlets respectively for admitting respiratory gas and for admitting the oxygen containing gas or the air. Alternatively the chamber may be provided with a single inlet which is coupled through separate control valves to the source of respiratory gas and to for example, the air source.

In a preferred embodiment of the invention, an electric signal representative of threshold carbon dioxide level is translated to a form suitable for storage in a memory device. Correction for threshold carbon dioxide level conveniently is achieved by subsequently subtracting the stored signal from the operational signal derived from the mass spectrometer and indicative of carbon dioxide measured during respiration.

Figure 2:
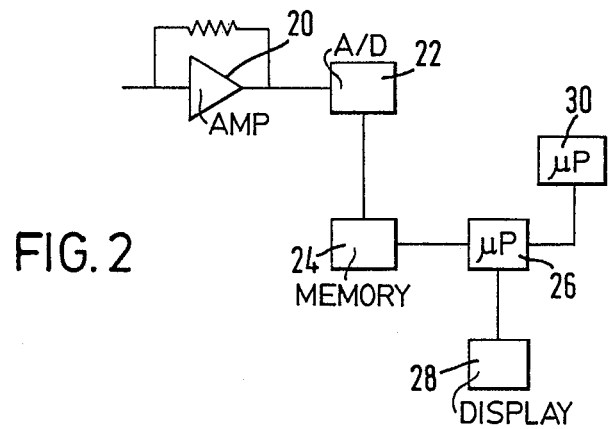

An embodiment of the invention will now be particularly described by way of example with reference to the accompanying drawings in which:

FIG. 1 is a block diagram of a mass spectrometer adapted in accordance with the present invention for detecting inter alia respiratory carbon dioxide and FIG. 2 is a block diagram of an electrical circuit for measuring the level inter alia of carbon dioxide detected by the mass spectrometer of FIG. 1.

Referring to FIG. 1 of the drawings, this illustrates a mass spectrometer of known kind indicated generally at 2. The mass spectrometer may be of the kind in which electrostatic or magnetic deflection occurs of ions produced by collision of gas introduced for analysis into the mass spectrometer chamber 4, with electrons accelerated from a heated element (not shown).

The mass spectrometer chamber 4 is evacuated to a pressure typically of less than $10^{-1}$ millibars by a rotary pump 6 which backs a diffusion or other low pressure pump 8 of any type well known in the art. A needle valve or other controlled leak 10 communicates with the chamber 4 to permit the bleed into the mass spectrometer, of the gas to be analysed.

In accordance with the present invention, the gas to be analysed is respiratory gas specifically but not necessarily from a patient undergoing anaesthesia and will include carbon dioxide as a component of variable concentration. Respiratory gas is accordingly derived from the patient and bled into mass spectrometer chamber 4 through inlet 12 by way of flow shut off valve 14; the concentration inter alia of carbon dioxide is obtained in known manner by tuning or otherwise setting the mass spectrometer and measuring the anode current.

Carbon dioxide present in chamber 4 will include in addition to respiratory carbon dioxide obtained friom the patient, a threshold level arising from the oxidation of hydrocarbon or other carbon containing vapours emitted by or through the diffusion lamp 8. This threshold level represents an error from the true value of carbon dioxide respired by the patient and must accordingly be corrected for.

In accordance with the present invention, such correction is obtained by intermittently interrupting the flow of respiratory gas to the mass spectrometer by shut off valve 14 and introducing into the mass spectrometer, an oxygen containing gas, such as air, substantially free of carbon dioxide. This gas is introduced to the mass spectrometer by way of an independent inlet 16 and shut off valve 18 although a common inlet controlled by two separaate shut-off valves may be employed.

Free oxygen from the air selectively admitted into the chamber 4 will combine with the hydrocarbon or other carbon containing vapours to produce a threshold level of carbon dioxide which will be detected by the mass spectrometer and will be represented by a threshold anode current.

The threshold and respiratory anode currents are measured and corrected for in the circuit shown in FIG. 2 In this figure, the anode current which is in analogue form is converted to a voltage signal in amplifier 20 and is translated to digital form in the analogue to digital converter 22.

The digital signal from converter 22 is applied to a memory storage device 24 which is arranged to store only the signal from the mass spectrometer during the period in which air is bled into the chamber 4 through the inlet/shut off valve combination 16, 18.

During the period when the mass spectrometer is used to analyse respiratory gas, the threshold signal stored in memory 22 is combined with the operational signal in a microprocessor 26, the output of which is applied to a display unit 28. The carbon dioxide level indicated by the display unit 28 will accordingly be corrected by the threshold level by suitable subtraction in the microprocessor 30.

A valve control system controller by the microprocessor 28 is effective to operate valves 14 and 18 to ensure that the respiratory gas and the air are introduced to the mass spectrometer at the appropriate times.

I claim:

1. A mass spectrometer for detecting the level of carbon dioxide in respiratory gases comprising a pumping system, a mass spectrometer chamber including means to selectively and intermittently receive the respiratory gas or a known concentration of oxygen of an oxygen containing gas substantially free of carbon dioxide, said mass spectrometer including means to detect the level of carbon dioxide in said respiratory gases when said respiratory gases are received by said spectrometer chamber and also to detect a threshold level of carbon dioxide in said oxygen containing gas when said oxygen containing gas is received by said mass spectrometer chamber, wherein said oxygen containing gas has a sufficient amount of oxygen to react with substantially all of the hydrocarbons produced by the pumping system to produce carbon dioxide, and means for correcting the detected level of carbon dioxide in said respiratory gases by subtracting said threshold level detected during the period when the mass spectrometer is responsive only to the oxygen containing gas.

2. A mass spectrometer as claimed in claim 1, including two valve means for selectively admitting respiratory gas and the oxygen containing gas to said mass spectrometer chamber.

3. A mass spectrometer as claimed in claim 1, comprising a single inlet means connected to two control valve means respectively for admitting respiratory gas and the oxygen containing gas to said mass spectrometer chamber.

4. A mass spectrometer as claimed in claim 1 or claim 2, wherein leak valve means are used to control the rate of gas flow into said mass spectrometer chamber.

5. A mass spectrometer as claimed in claim 4, wherein said leak valve means are needle valves.

6. A mass spectrometer as claimed in claim 1 including signal means to generate signal representative of the detected level of carbon dioxide in said spectrometer chamber of said respiratory gases and said detected threshold level of carbon dioxide in said oxygen containing gas, and said means for correcting for the threshold level of carbon dioxide during respiration comprises a signal translation circuit responsive to a signal representative of respiratory gases and producing an output signal indicative of respiratory carbon dioxide content, the signal translation circuit including a memory device effective to store the signal from the mass spectrometer representative of threshold carbon dioxide level.

7. A mass spectrometer as claimed in claim 6, wherein the output signal from the signal translation circuit is compensated by the signal stored in the memory device.

8. A mass spectrometer as claimed in claim 6 or claim 7, wherein the signal translation circuit is embodied in a microprocessor.

9. A mass spectrometer as claimed in claim 8, wherein the microprocessor is arranged to control a control valve means selectively admitting respiratory gas and the oxygen containing gas to the mass spectrometer chamber.

10. A method for monitoring respiratory gases with a mass spectrometer having a pumping system and a mass spectrometer chamber, comprising the steps of determining the level of carbon dioxide of a respiratory gas, intermittently applying to said mass spectrometer chamber, in the absence of the respiratory gas, a known concentration of oxygen in an oxygen containing gas substantially free of carbon dioxide so as to enable the oxygen to combine with substantially all of the residual carbon containing compounds derived from or through the pumping system to produce carbon dioxide for the mass spectrometer, determining the threshold level of carbon dioxide of said oxygen containing gas, and correcting the level of carbon dioxide measured in the respiratory gas by the threshold level measured in said oxygen containing gas.

11. A method as claimed in claim 10, wherein the respiratory gas and the oxygen containing gas are bled into the mass spectrometer chamber through leak control valves.

12. A method as claimed in claim 11, wherein the leak control valves are needle valves.

13. A method as claimed in claim 10 or claim 11, wherein an electrical signal representative of the threshold level of carbon dioxide is generated and stored in a memory device embodied in a signal translation circuit responsive to the output from the mass spectrometer and is utilised to compensate the output signal from the signal translation circuit to be indicative of the carbon dioxide content of the respiratory gas.

14. A method as claimed in claim 13, wherein a microprocessor incorporating the signal translation circuit is used to control the admission of respiratory gas and the oxygen containing gas into the mass spectrometer chamber.

* * * * *